(12) United States Patent
Zur et al.

(10) Patent No.: US 10,492,923 B2
(45) Date of Patent: Dec. 3, 2019

(54) EXPANDING IMPLANT WITH HINGED ARMS

(71) Applicant: SEASPINE, INC., Carlsbad, CA (US)

(72) Inventors: Gal Zur, Petah Tikwa (IL); Haim Yustein, Netanya (IL)

(73) Assignee: SEASPINE, INC., Carlsbad, CA (US)

( * ) Notice: Subject to any disclaimer, the term of this patent is extended or adjusted under 35 U.S.C. 154(b) by 225 days.

(21) Appl. No.: 15/322,110

(22) PCT Filed: Jun. 25, 2015

(86) PCT No.: PCT/IL2015/050664
§ 371 (c)(1),
(2) Date: Dec. 25, 2016

(87) PCT Pub. No.: WO2015/198335
PCT Pub. Date: Dec. 30, 2015

(65) Prior Publication Data
US 2017/0156885 A1    Jun. 8, 2017

Related U.S. Application Data

(60) Provisional application No. 62/016,689, filed on Jun. 25, 2014.

(51) Int. Cl.
*A61F 2/44* (2006.01)
*A61F 2/30* (2006.01)

(52) U.S. Cl.
CPC .... *A61F 2/447* (2013.01); *A61F 2002/30434* (2013.01); *A61F 2002/30471* (2013.01);
(Continued)

(58) Field of Classification Search
CPC .............. A61F 2/447; A61F 2/4455; A61F 2002/4475; A61F 2002/30471
See application file for complete search history.

(56) References Cited

U.S. PATENT DOCUMENTS 4,755,769 A    7/1988  Katz
5,059,193 A   10/1991  Kuslich
(Continued)

FOREIGN PATENT DOCUMENTS

DE    2263842    7/1974
DE    9107494    9/1991
(Continued)

OTHER PUBLICATIONS

Alici E, Alli OZ, Dost S. "Prostheses designed for vertebral body replacement", J Biomech. 1990;23(8):799-809.

*Primary Examiner* — Amy R Sipp
(74) *Attorney, Agent, or Firm* — Middleton Reutlinger

(57) ABSTRACT

An implant (500, 600) includes first and second arms (14a, 14b) hinged to a base (12) at spaced-apart locations. An actuator (18, 22a, 22b, 602, 604, 606) is deployed to rotate the arms from an initial position in opposing angular motion towards a final position. A rigid bridging element (28) bridges between the arms so that deployment of the arms towards the final position displaces the bridging element away from the base. Engagement between the bridging element and at least one of the arms is via a double pin-in-slot engagement in which two non-collinear pins (30, 40) are engaged in respective non-parallel slots (32, 42).

17 Claims, 11 Drawing Sheets

(52) U.S. Cl.
CPC ............... *A61F 2002/30492* (2013.01); *A61F 2002/30525* (2013.01); *A61F 2002/30579* (2013.01); *A61F 2002/4475* (2013.01)

(56) References Cited

U.S. PATENT DOCUMENTS

| | | | |
|---|---|---|---|
| 5,171,278 A | 12/1992 | Pisharodi | |
| 5,258,031 A | 11/1993 | Salib et al. | |
| 5,390,683 A | 2/1995 | Pisharodi | |
| 5,520,458 A | 5/1996 | Arutyunov et al. | |
| 5,534,029 A | 7/1996 | Shima | |
| 5,599,279 A | 2/1997 | Slotman et al. | |
| 6,039,761 A | 3/2000 | Li et al. | |
| 6,080,193 A | 6/2000 | Hochshuler et al. | |
| 6,126,680 A | 10/2000 | Wass | |
| 6,126,689 A | 10/2000 | Brett | |
| 6,190,414 B1 | 2/2001 | Young et al. | |
| 6,193,757 B1 | 2/2001 | Foley | |
| 6,238,403 B1 | 5/2001 | Greene, Jr. et al. | |
| 6,332,894 B1 | 12/2001 | Stalcup et al. | |
| 6,368,351 B1 | 4/2002 | Glenn | |
| 6,375,682 B1 | 4/2002 | Fleischmann et al. | |
| 6,419,705 B1 | 7/2002 | Erickson | |
| 6,443,989 B1 | 9/2002 | Jackson | |
| 6,491,724 B1 | 12/2002 | Ferree | |
| 6,576,016 B1 | 6/2003 | Hochshuler et al. | |
| 6,582,451 B1 | 6/2003 | Marucci et al. | |
| 6,620,196 B1 | 9/2003 | Trieu | |
| 6,641,614 B1 | 11/2003 | Wagner et al. | |
| 6,676,665 B2 | 1/2004 | Foley et al. | |
| 6,706,070 B1 | 3/2004 | Wagner et al. | |
| 6,830,588 B2 | 12/2004 | Furukawa et al. | |
| 6,830,589 B2 | 12/2004 | Erickson | |
| 6,993,808 B1 * | 2/2006 | Bennett | A61F 5/0125 16/321 |
| 7,070,598 B2 | 7/2006 | Lim et al. | |
| 7,087,055 B2 | 8/2006 | Lim et al. | |
| 7,097,648 B1 | 8/2006 | Globerman et al. | |
| 7,431,735 B2 | 10/2008 | Liu et al. | |
| 7,621,956 B2 | 11/2009 | Paul | |
| 7,625,377 B2 | 12/2009 | Veldhuizen et al. | |
| 7,641,690 B2 | 1/2010 | Abdoiu | |
| 7,655,046 B2 | 2/2010 | Dryer et al. | |
| 7,720,282 B2 | 5/2010 | Blake et al. | |
| 7,763,028 B2 | 7/2010 | Lim et al. | |
| 7,790,981 B2 | 9/2010 | Vaupotic et al. | |
| 7,846,206 B2 | 12/2010 | Oglaza et al. | |
| 7,850,734 B2 | 12/2010 | Oh | |
| 7,901,409 B2 | 3/2011 | Canaveral et al. | |
| 7,905,920 B2 | 3/2011 | Galea | |
| 7,909,872 B2 | 3/2011 | Zipnick et al. | |
| 7,938,860 B2 | 5/2011 | Trieu | |
| 7,947,078 B2 | 5/2011 | Siegal | |
| 7,959,652 B2 | 6/2011 | Zucherman et al. | |
| 8,021,429 B2 | 9/2011 | Viker | |
| 8,025,665 B2 | 9/2011 | Lim et al. | |
| 8,062,375 B2 | 11/2011 | Glerum et al. | |
| 8,100,972 B1 | 1/2012 | Bruffey | |
| 8,123,809 B2 | 2/2012 | Melkent et al. | |
| 8,133,232 B2 | 3/2012 | Levy et al. | |
| 8,187,332 B2 | 3/2012 | Moluen | |
| 8,241,358 B2 | 8/2012 | Butler | |
| 8,292,963 B2 | 10/2012 | Miller et al. | |
| 8,303,658 B2 | 11/2012 | Peterman | |
| 8,308,802 B2 | 11/2012 | Rhoda et al. | |
| 8,317,786 B2 | 11/2012 | Dahla et al. | |
| 8,317,798 B2 | 11/2012 | Lim | |
| 8,317,802 B1 | 11/2012 | Manzi et al. | |
| 8,317,866 B2 | 11/2012 | Palmatier et al. | |
| 8,323,344 B2 | 12/2012 | Galeey et al. | |
| 8,337,531 B2 | 12/2012 | Johnson et al. | |
| 8,337,559 B2 | 12/2012 | Hansell et al. | |
| 8,343,193 B2 | 1/2013 | Johnson et al. | |
| 8,349,013 B2 | 1/2013 | Zucherman et al. | |
| 8,349,014 B2 | 1/2013 | Barreiro et al. | |
| 8,377,071 B2 | 2/2013 | Lim et al. | |
| 8,398,713 B2 | 3/2013 | Weiman | |
| 8,403,990 B2 | 3/2013 | Dryer et al. | |
| 8,444,697 B1 | 5/2013 | Butler et al. | |
| 8,518,120 B2 | 8/2013 | Glerum et al. | |
| 8,523,944 B2 | 9/2013 | Jimenez | |
| 8,556,979 B2 | 10/2013 | Glerum et al. | |
| 8,579,907 B2 | 11/2013 | Lim et al. | |
| 8,628,576 B2 | 1/2014 | Triplett et al. | |
| 8,628,577 B1 | 1/2014 | Jimenez | |
| 8,679,183 B2 | 3/2014 | Glerum et al. | |
| 8,685,098 B2 | 4/2014 | Glerum et al. | |
| 8,709,086 B2 | 4/2014 | Glerum | |
| 8,771,360 B2 | 7/2014 | Jimenez | |
| 8,777,993 B2 | 7/2014 | Siegal et al. | |
| 8,870,959 B2 | 10/2014 | Arnin | |
| 8,940,049 B1 * | 1/2015 | Jimenez | A61F 2/447 623/17.15 |
| 9,017,413 B2 | 4/2015 | Siegal | |
| 9,138,328 B2 | 9/2015 | Butler et al. | |
| 9,532,883 B2 | 1/2017 | Mcluen et al. | |
| 2003/0236520 A1 | 12/2003 | Lim et al. | |
| 2004/0044411 A1 | 3/2004 | Suddaby | |
| 2004/0059418 A1 | 3/2004 | Mckay et al. | |
| 2004/0133280 A1 | 7/2004 | Trieu | |
| 2004/0162618 A1 | 8/2004 | Mujwid et al. | |
| 2004/0193158 A1 | 9/2004 | Lim et al. | |
| 2005/0033431 A1 | 2/2005 | Gordon et al. | |
| 2005/0060036 A1 | 3/2005 | Schultz | |
| 2005/0113920 A1 | 5/2005 | Foley et al. | |
| 2005/0125062 A1 | 6/2005 | Biedermann et al. | |
| 2005/0143827 A1 | 6/2005 | Globerman et al. | |
| 2005/0182416 A1 | 8/2005 | Lim et al. | |
| 2005/0209698 A1 | 9/2005 | Gordon | |
| 2005/0228391 A1 | 10/2005 | Levy et al. | |
| 2005/0261683 A1 | 11/2005 | Veldhuizen et al. | |
| 2005/0278036 A1 | 12/2005 | leonard et al. | |
| 2006/0004455 A1 | 1/2006 | Leonard et al. | |
| 2006/0041258 A1 | 2/2006 | Galea | |
| 2006/0085070 A1 | 4/2006 | Kim | |
| 2006/0142858 A1 | 6/2006 | Colleran et al. | |
| 2006/0224241 A1 | 10/2006 | Butler et al. | |
| 2006/0235423 A1 * | 10/2006 | Cantu | A61B 17/8858 606/90 |
| 2006/0247776 A1 | 11/2006 | Kim | |
| 2006/0247778 A1 | 11/2006 | Ferree | |
| 2007/0032791 A1 | 2/2007 | Greenhalgh | |
| 2007/0073398 A1 | 3/2007 | Fabian et al. | |
| 2007/0123986 A1 | 5/2007 | Schaller | |
| 2007/0173939 A1 | 7/2007 | Kim et al. | |
| 2007/0233245 A1 | 10/2007 | Trieu et al. | |
| 2007/0260314 A1 | 11/2007 | Biyani | |
| 2007/0282449 A1 | 12/2007 | De Villiers et al. | |
| 2008/0119853 A1 | 5/2008 | Felt et al. | |
| 2008/0125865 A1 | 5/2008 | Abdelgany | |
| 2008/0243255 A1 | 10/2008 | Buttler et al. | |
| 2008/0249628 A1 | 10/2008 | Altarac | |
| 2008/0312743 A1 | 12/2008 | Vila et al. | |
| 2009/0093882 A1 | 4/2009 | Oh | |
| 2009/0157186 A1 | 6/2009 | Magerl | |
| 2009/0216274 A1 | 8/2009 | Morancy-Meister et al. | |
| 2009/0270873 A1 | 10/2009 | Fabian | |
| 2009/0299478 A1 | 12/2009 | Carls et al. | |
| 2010/0131009 A1 | 5/2010 | Roebling et al. | |
| 2010/0211176 A1 | 8/2010 | Greenhalgh | |
| 2010/0256764 A1 | 10/2010 | Tsuang et al. | |
| 2010/0274357 A1 | 10/2010 | Miller et al. | |
| 2010/0286787 A1 | 11/2010 | Villiers et al. | |
| 2011/0054537 A1 | 3/2011 | Miller | |
| 2011/0125270 A1 | 5/2011 | Paul | |
| 2011/0138948 A1 | 6/2011 | Jimenez et al. | |
| 2011/0172710 A1 | 7/2011 | Thommen et al. | |
| 2011/0172719 A1 | 7/2011 | Gorhan et al. | |
| 2011/0276141 A1 | 11/2011 | Caratsch | |
| 2012/0004732 A1 | 1/2012 | Goel et al. | |
| 2012/0025941 A1 | 2/2012 | Wang et al. | |
| 2012/0053642 A1 | 3/2012 | Lozier | |
| 2012/0083889 A1 | 4/2012 | Purcell et al. | |
| 2012/0123546 A1 | 5/2012 | Medina | |

(56) References Cited

U.S. PATENT DOCUMENTS

| | | |
|---|---|---|
| 2012/0165944 A1 | 6/2012 | McGuckin, Jr. |
| 2012/0209386 A1 | 8/2012 | Triplett et al. |
| 2012/0221107 A1 | 8/2012 | Sack et al. |
| 2012/0259416 A1 | 10/2012 | Blackwell et al. |
| 2012/0271422 A1 | 10/2012 | Miller et al. |
| 2012/0277866 A1 | 11/2012 | Kalluri et al. |
| 2013/0015856 A1 | 1/2013 | Weinberg |
| 2013/0041471 A1 | 2/2013 | Siegal et al. |
| 2013/0066374 A1 | 3/2013 | Galeey et al. |
| 2013/0079883 A1 | 3/2013 | Butler et al. |
| 2013/0144391 A1 | 6/2013 | Siegal et al. |
| 2013/0158664 A1 | 6/2013 | Palmatier |
| 2013/0158669 A1 | 6/2013 | Sungarian et al. |
| 2013/0190876 A1* | 7/2013 | Drochner ............. A61F 2/442 623/17.16 |
| 2013/0274883 A1 | 10/2013 | McLuen et al. |
| 2013/0317615 A1 | 11/2013 | Jimenez et al. |
| 2013/0325128 A1 | 12/2013 | Perloff et al. |
| 2014/0018822 A1 | 1/2014 | Main |
| 2014/0052254 A1 | 2/2014 | Glerum et al. |
| 2014/0114429 A1 | 4/2014 | Slone et al. |
| 2014/0156007 A1 | 6/2014 | Pabst et al. |
| 2014/0243982 A1 | 8/2014 | Miller |
| 2014/0249628 A1 | 9/2014 | Weiman |
| 2014/0249629 A1 | 9/2014 | Moskowitz et al. |

FOREIGN PATENT DOCUMENTS

| | | |
|---|---|---|
| DE | 4416605 | 6/1995 |
| FR | 2717068 | 9/1995 |
| JP | 2004530527 | 10/2004 |
| JP | 2008512218 | 4/2008 |
| JP | 2011120957 | 6/2011 |
| WO | 98/34552 | 8/1998 |
| WO | 03003951 | 1/2003 |
| WO | 2006050500 | 5/2006 |
| WO | 2008044057 | 4/2008 |
| WO | 2008084479 | 7/2008 |
| WO | 2008103781 | 8/2008 |
| WO | 2012011078 | 7/2011 |
| WO | 2012112596 | 8/2012 |
| WO | 2013052807 | 4/2013 |
| WO | 2013109346 | 7/2013 |
| WO | 2013133729 | 9/2013 |
| WO | 2013158294 | 10/2013 |

* cited by examiner

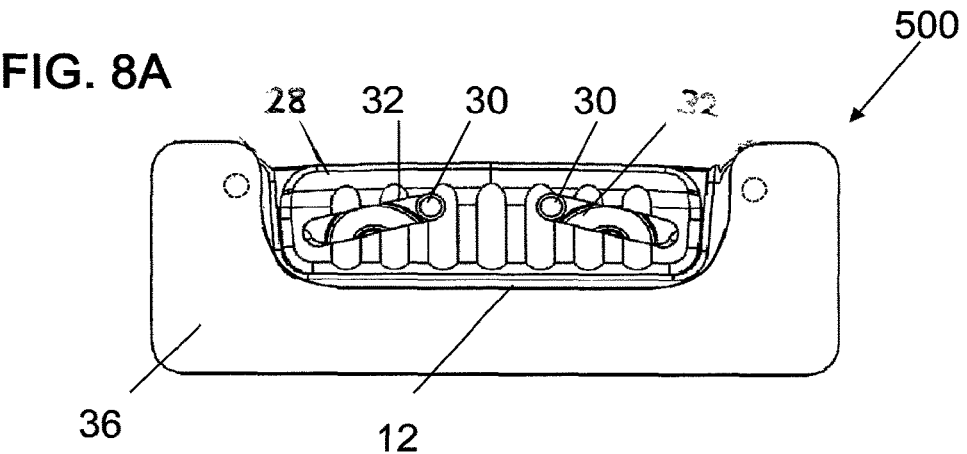
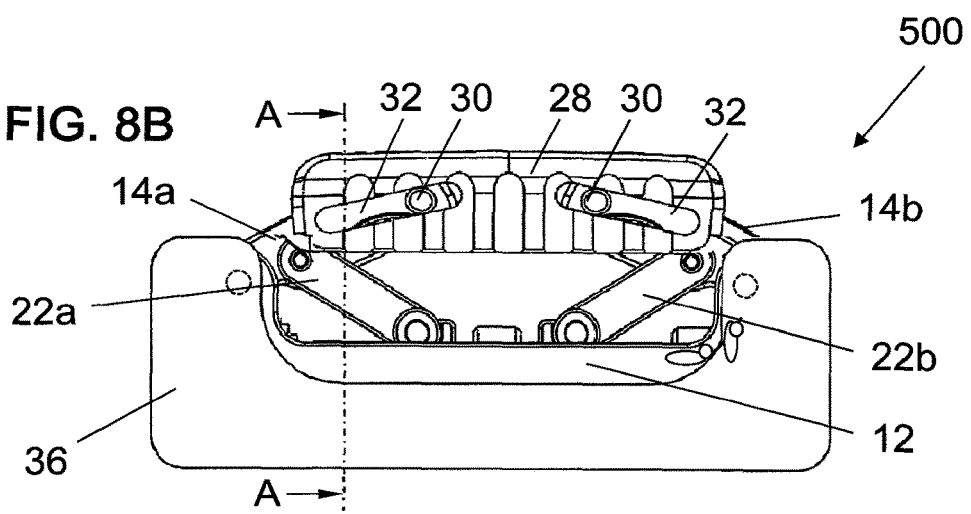
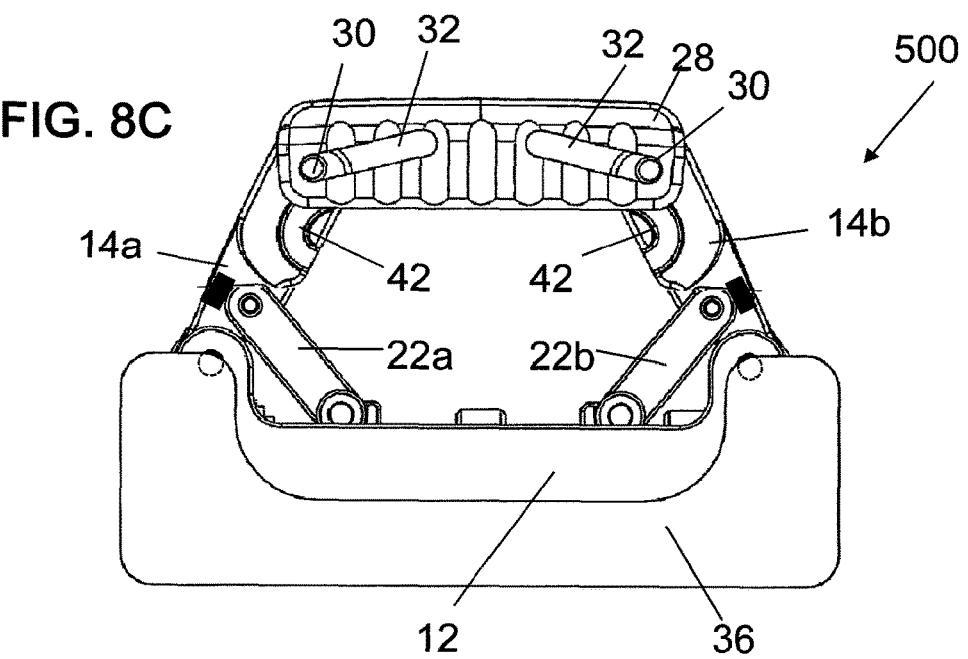

EXPANDING IMPLANT WITH HINGED ARMS

FIELD AND BACKGROUND OF THE INVENTION

The present invention relates to orthopedic implants and, in particular, it concerns an expanding implant with hinged arms.

It is known to provide various types of orthopedic implant which change form after insertion, typically to allow introduction of the implant into the body in a collapsed or small-cross-section form prior to deployment of the implant within the body. Various deployment mechanisms are used to effect the change of form during or after introduction of the implant into the body.

SUMMARY OF THE INVENTION

The present invention is an expanding implant with hinged arms.

According to the teachings of an embodiment of the present invention there is provided, an implant comprising: (a) a base; (b) a first arm hinged to the base at a first hinge location and extending from the first hinge location in a direction of extension; (c) a second arm hinged to the base at a second hinge location and extending from the second hinge location in a direction of extension, the first and second arms assuming an initial state; (d) an actuator operatively linked to the first and second arms and operable to rotate the first and second arms from the initial state in opposing angular motion towards a final state; and (e) a rigid bridging element bridging between the first arm and the second arm such that deployment of the first and second arms from the initial state towards the final state displaces the bridging element away from the base, wherein engagement between the bridging element and at least one of the first and second arms is via a double pin-in-slot engagement with two non-collinear pins engaged in respective non-parallel slots.

According to a further feature of an embodiment of the present invention, the double pin-in-slot engagement comprises a first pin projecting from the first arm engaging a slot formed in the bridging element, and a pin projecting from the bridging element engaging a slot formed in the first arm.

According to a further feature of an embodiment of the present invention, engagement between the bridging element and each of the first and second arms is via a double pin-in-slot engagement with two non-collinear pins engaged in respective non-parallel slots.

According to a further feature of an embodiment of the present invention, the actuator comprises: (a) a threaded bolt extending within the base and mounted so as to be rotatable about a central axis of the threaded bolt; (b) a first actuator linkage hinged to the first arm and hinged to a first rider engaged with the threaded bolt; and (c) a second actuator linkage hinged to the second arm and hinged to a second rider engaged with the threaded bolt, such that rotation of the threaded bolt causes displacement of the first and second riders, and hence of the first and second actuator linkages to generate motion of the first and second arms.

According to a further feature of an embodiment of the present invention, the first actuator linkage and the second actuator linkage are of different lengths such that the bridging element opens asymmetrically away from the base.

According to a further feature of an embodiment of the present invention, each of the first and second arms is hinged to the base at a hinge location, and extends from the hinge location in a direction of extension, the directions of extension of the first and second arms being convergent.

According to a further feature of an embodiment of the present invention, the first arm further comprises a rear projection projecting beyond the hinge location in a direction away from the direction of extension, the implant further comprising a displaceable portion engaged with the rear projection such that rotation of the threaded bolt causes displacement of the bridging element in a first direction and of the displaceable portion in a second direction generally opposite to the first direction.

According to a further feature of an embodiment of the present invention, the displaceable portion is pivotally linked to the base.

According to a further feature of an embodiment of the present invention, each of the first and second arms further comprises a rear projection projecting beyond the hinge location in a direction away from the direction of extension, the implant further comprising a displaceable portion engaged with the rear projections such that rotation of the threaded bolt causes displacement of the bridging element in a first direction and of the displaceable portion in a second direction generally opposite to the first direction.

According to a further feature of an embodiment of the present invention, the threaded bolt includes a first portion with a right-handed thread and a second portion with a left-handed thread.

There is also provided according to the teachings of an embodiment of the present invention, an implant comprising: (a) a base; (b) a first arm hinged to the base; (c) a second arm hinged to the base; (d) a threaded bolt extending within the base and mounted so as to be rotatable about a central axis of the threaded bolt; (e) a first actuator linkage hinged to the first arm and hinged to a first rider engaged with the threaded bolt; and (f) a second actuator linkage hinged to the second arm and hinged to a second rider engaged with the threaded bolt, such that rotation of the threaded bolt causes displacement of the first and second riders, and hence of the first and second actuator linkages to generate motion of the first and second arms.

According to a further feature of an embodiment of the present invention, there is also provided a bridging element bridging between the first arm and the second arm.

According to a further feature of an embodiment of the present invention, the bridging element is a rigid bridging element engaged with the first and second arms by a pin-in-slot engagement.

According to a further feature of an embodiment of the present invention, the pin-in-slot engagement is a double-pin-in-slot engagement with two pins engaged in non-parallel slots.

According to a further feature of an embodiment of the present invention, the first actuator linkage and the second actuator linkage are of different lengths such that the bridging element opens asymmetrically away from the base.

According to a further feature of an embodiment of the present invention, each of the first and second arms is hinged to the base at a hinge location, and extends from the hinge location in a direction of extension, the directions of extension of the first and second arms being convergent.

According to a further feature of an embodiment of the present invention, the first arm further comprises a rear projection projecting beyond the hinge location in a direction away from the direction of extension, the implant further comprising a displaceable portion engaged with the rear projection such that rotation of the threaded bolt causes displacement of the bridging element in a first direction and of the displaceable portion in a second direction generally opposite to the first direction.

According to a further feature of an embodiment of the present invention, the displaceable portion is pivotally linked to the base.

According to a further feature of an embodiment of the present invention, each of the first and second arms further comprises a rear projection projecting beyond the hinge location in a direction away from the direction of extension, the implant further comprising a displaceable portion engaged with the rear projections such that rotation of the threaded bolt causes displacement of the bridging element in a first direction and of the displaceable portion in a second direction generally opposite to the first direction.

According to a further feature of an embodiment of the present invention, the threaded bolt includes a first portion with a right-handed thread and a second portion with a left-handed thread.

There is also provided according to the teachings of an embodiment of the present invention, an implant comprising: (a) a base having a length; (b) a first arm hinged to the base at a hinge location and extending from the hinge location in a direction of extension, the first arm assuming an initial state in which the direction of extension is at a first angle to the length, the first arm further comprising a rear projection projecting beyond the hinge location in a direction away from the direction of extension; (c) an actuator operatively linked to the first arm and operable to rotate the first arm from the initial state towards a deployed state in which the direction of extension is at a second angle to the length greater than the first angle; and (d) a displaceable portion engaged with the rear projection such that rotation of the first arm from the initial state towards the deployed state causes displacement of the displaceable portion relative to the base.

According to a further feature of an embodiment of the present invention, the displaceable portion is pivotally linked to the base.

According to a further feature of an embodiment of the present invention, there is also provided a second arm hinged to the base at a second hinge location and extending from the hinge location in a direction of extension, the directions of extension of the first and second arms converging in the initial state, the actuator being configured to rotate the second arm in an angular direction opposite to rotation of the first arm.

According to a further feature of an embodiment of the present invention, the second arm further comprises a rear projection projecting beyond the second hinge location in a direction away from the direction of extension, and wherein the displaceable portion is additionally engaged with the rear projection of the second arm.

According to a further feature of an embodiment of the present invention, there is also provided a bridging element bridging between the first arm and the second arm.

According to a further feature of an embodiment of the present invention, the displaceable portion is implemented as a casing at least partially encompassing the base.

BRIEF DESCRIPTION OF THE DRAWINGS

The invention is herein described, by way of example only, with reference to the accompanying drawings, wherein:

FIGS. 8A-8C are side views of a modified version of the implant of FIGS. 1A-1C illustrating a further aspect of the present invention for limiting sliding of a bridging element bridging between the arms, the implant being shown in a low-profile insertion state, a partially-expanded state and a fully-expanded state, respectively;

DESCRIPTION OF THE PREFERRED EMBODIMENTS

Figure 1A:
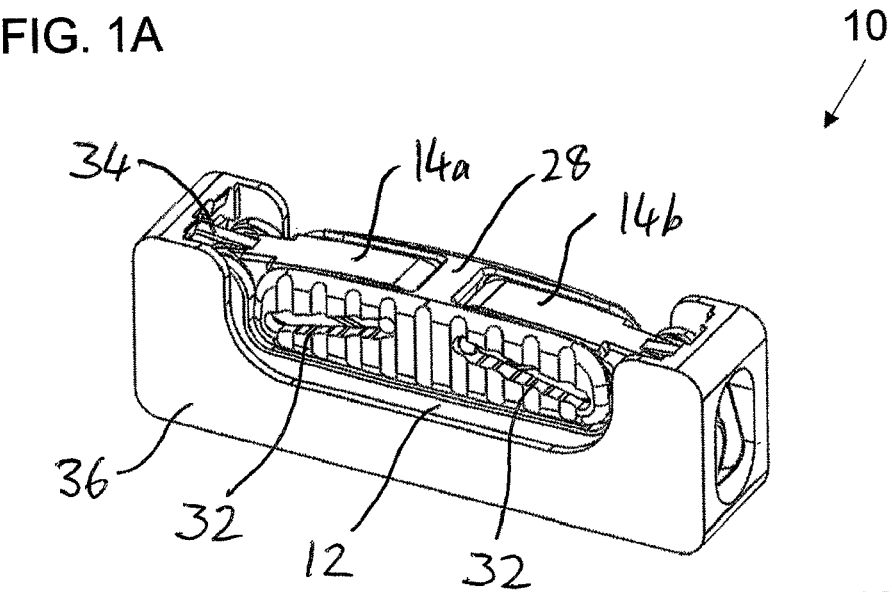
FIGS. 1A-1C are isometric views of an implant, constructed and operative according to an embodiment of the present invention, shown in a low-profile insertion state, a partially-expanded state and a fully-expanded state, respectively.
Figure 1B:
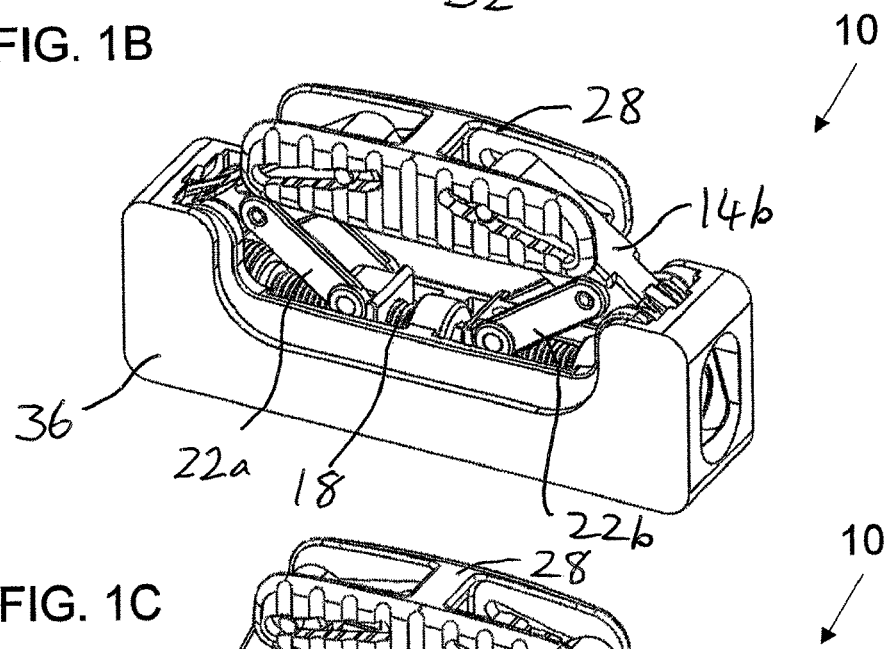

The present invention is an expanding implant with hinged arms.

By way of introduction, reference is made to a range of implants described in PCT Patent Application Publication No. WO2015087285 in which one or more arms are pivotally connected to a base and are deployable to expand the implant from an initial state for insertion to an expanded state within the body. The WO2015087285 publication, which is commonly owned with the present invention and was unpublished at the priority date of this application, is not admitted as prior art except where defined as such under the applicable local law.

The present invention relates to a number of variations, additions or improvements to the expanding implants described in the WO2015087285 publication particularly in three aspects, which are each of utility when used alone, but which may also be used to advantage in various combinations. A first aspect, exemplified herein with reference to the embodiments of FIGS. 1A-7B, relates to a deployment mechanism based on a threaded bolt arrangement. A second aspect relates to an additional displacement part (shown as a casing) which is deployed by rearward projections from the arms. This second aspect is also exemplified herein with reference to the embodiments of FIGS. 1A-7B. A third aspect of the invention relates to an arrangement of pin-in-slot engagements between the arms and a bridging element between the arms. This third aspect is relevant to all embodiments illustrated herein, and is illustrated herein in the context of two exemplary embodiments in FIGS. 8A-11C.

Turning now to the drawings, FIGS. 1A-3 illustrate an implant, generally designated 10, constructed and operative according to the teachings of an embodiment of the present invention. In general terms, implant 10 has a base 12, a first arm 14a hinged to the base at a hinge location 16a, and a second arm 14b hinged to the base at a hinge location 16b. According to a first aspect of the present invention, actuation of motion of the two arms is achieved by an actuator including a threaded bolt 18 extending within base 12 and mounted so as to be rotatable about a central axis 20 of threaded bolt 18. A first actuator linkage 22a is hinged to first arm 14a at a pivot point 24a and to a first threaded rider 26a engaged with threaded bolt 18. Similarly, a second actuator linkage 22a is hinged to second arm 14b at a pivot point 24b and to a second threaded rider 26b engaged with threaded bolt 18. In the configuration shown here, threaded bolt 18 includes a first portion 18a with a left-handed thread and a second portion 18b with a right-handed thread. These two portions may either be integrally formed as a single bolt, or bolt 18 may be assembled from two separate interlocked parts (as illustrated here). Rotation of threaded bolt 18 thus causes displacement of the first and second riders 26a, 26b in opposite directions. This motion displaces first and second actuator linkages 22a, 22b and hence generates motion of the first and second arms, reversibly, through the range of positions illustrated in FIGS. 1A-1C and 2A-2C.

It should be noted that the use of a threaded-bolt actuator in this context may offer considerable advantages of simplicity, reliability, reversibility and/or capacity to bear loads. However, in the case of a pair of arms, the range of motion for each rider is inherently limited to less than half the length of base 12, and in practical terms, may be limited to not significantly more than a quarter of the base length. The geometry of connection of actuator linkages 22a and 22b is therefore preferably chosen according to the teachings of certain embodiments of the present invention to achieve mechanical amplification, i.e., where the end portion of each arm moves a greater distance than motion of the corresponding rider along the bolt.

Figure 2A:
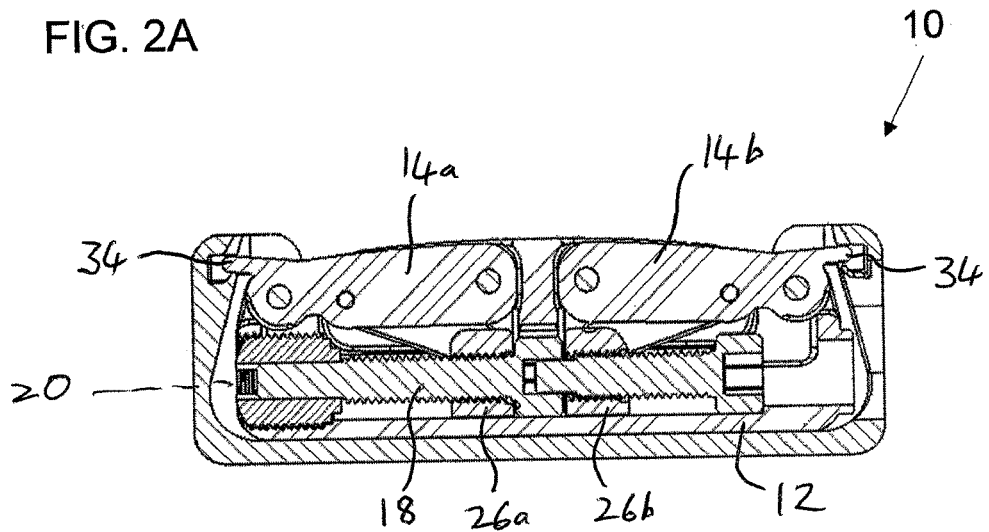
FIGS. 2A-2C are cross-sectional views taken through the implant of FIGS. 1A-1C in the states of FIGS. 1A-1C, respectively.
Figure 2B:
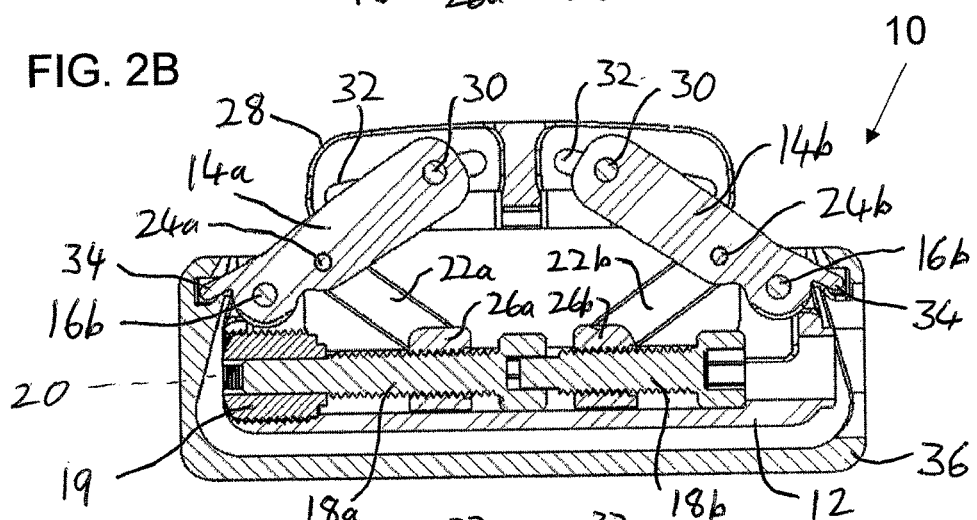
Figure 2C:
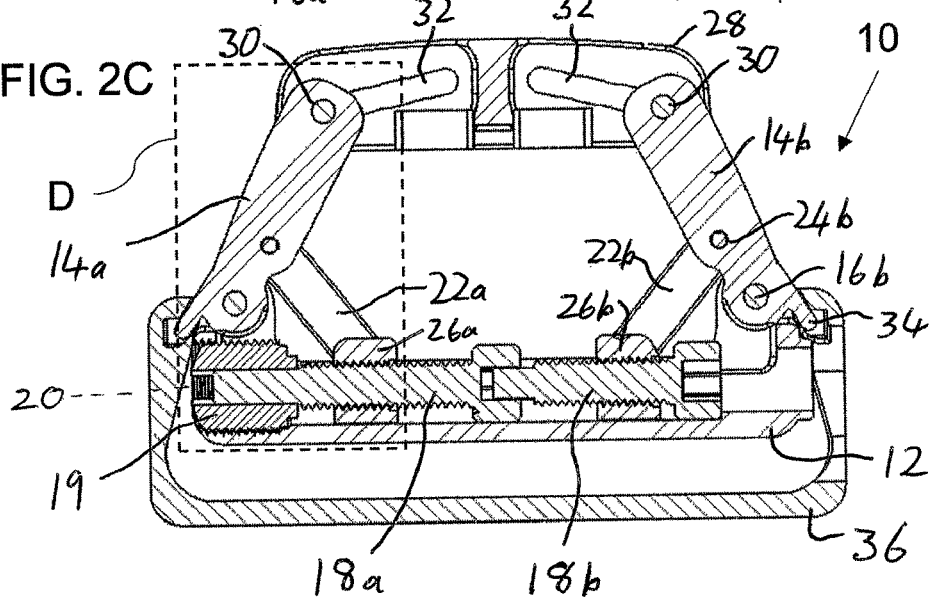
Figure 2D:
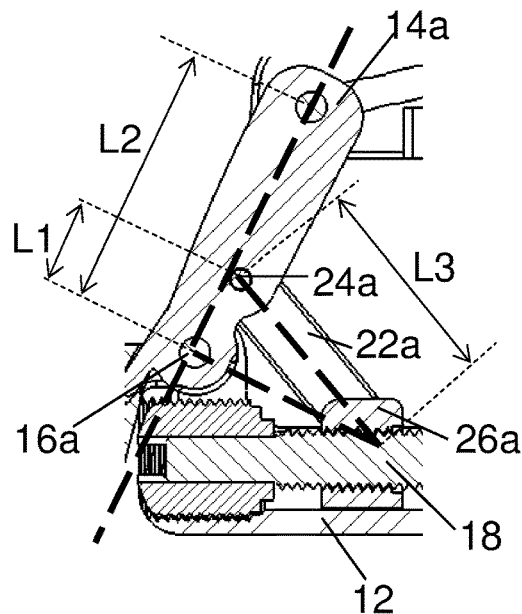
FIG. 2D is an enlarged view of the region of FIG. 2C identified by dashed rectangle "D"

Specifically, referring to FIG. 2D, a length $L_1$ from hinge location 16a to pivot point 24a is preferably less than half a length $L_2$ from hinge location 16a along a direction of extension of arm 14a to the end of the arm. Additionally, $L_1$ is preferably less than the length $L_3$ of actuator linkage 22a between its pivotal connection at pivot point 24a and its pivotal connection to rider 26a. The degree of mechanical amplification can be selected by suitable choice of the ratios of $L_1$, $L_2$ and $L_3$, and will vary according to the intended application, the range of motion required, the load expected to be encountered, the load that can be applied to turn the bolt, and the strength of the materials used. In certain particularly preferred implementations, a ratio of $L_1$ to $L_3$ in the range of 50%-95% is used. Where greater mechanical amplification is required, ratios in the range of 20%-50%, or in the range of 20%-33%, or in the range of 10%-25%, each provide particular advantages for a corresponding set of applications. For the sake of precision, it is noted that pivot point 24a does not necessarily lie on the dashed line illustrating the "extensional direction" of the arm. The dimensions used to define $L_1$ and $L_3$ are specifically the inter-axis distances.

Figure 4A:
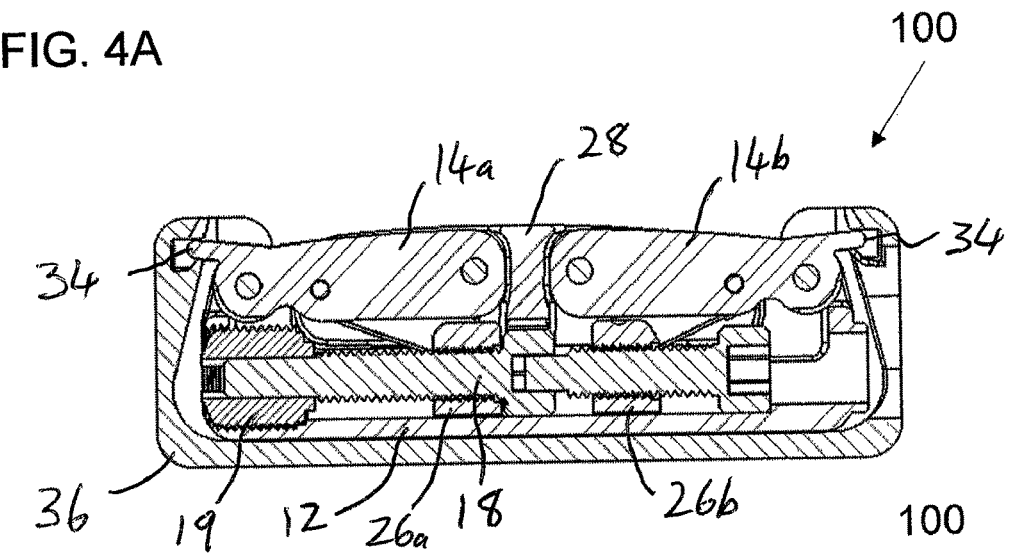
FIGS. 4A-4C are views similar to FIGS. 2A-2C illustrating a first variant implementation of the implant of FIGS. 1A-1C having asymmetric expansion.
Figure 4B:
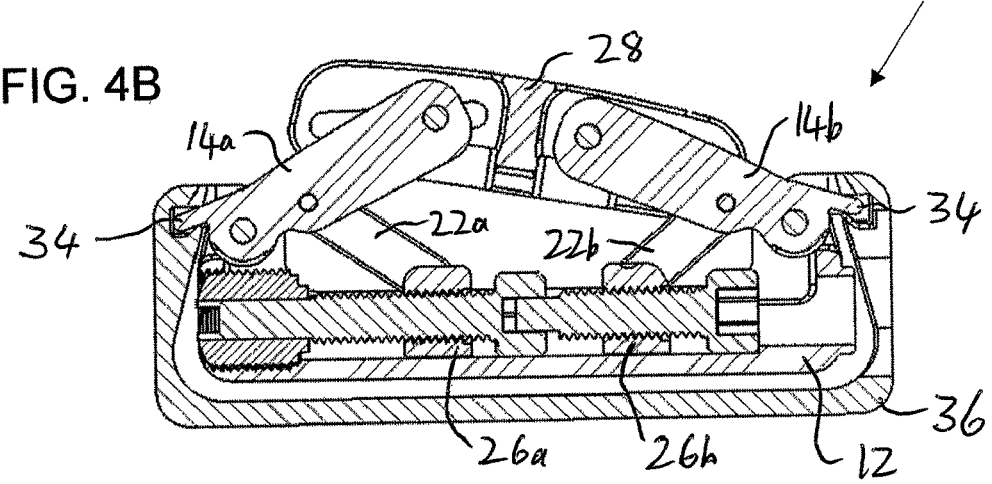
Figure 4C:
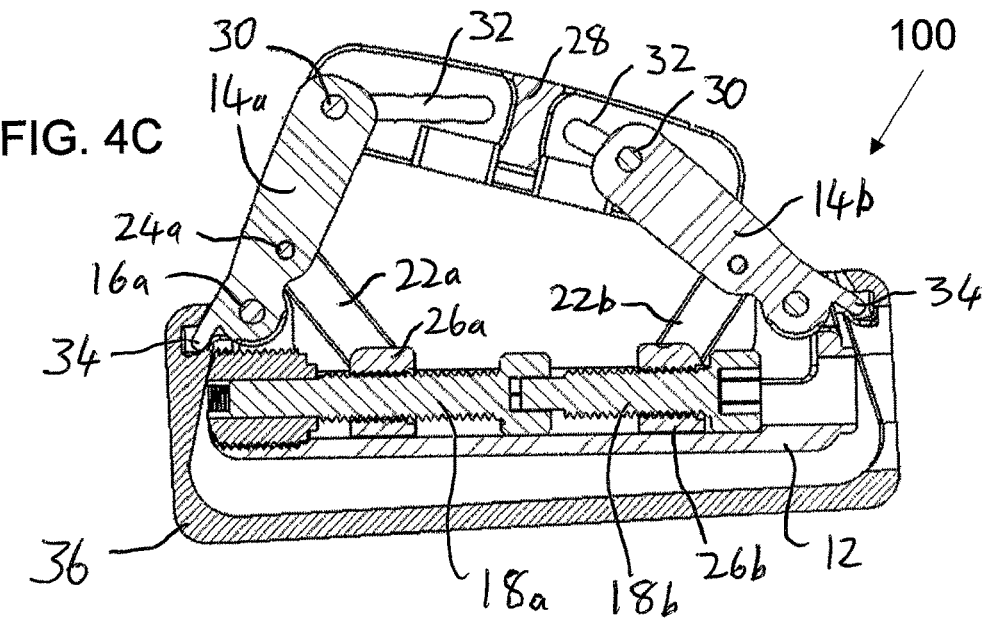
Figure 5A:
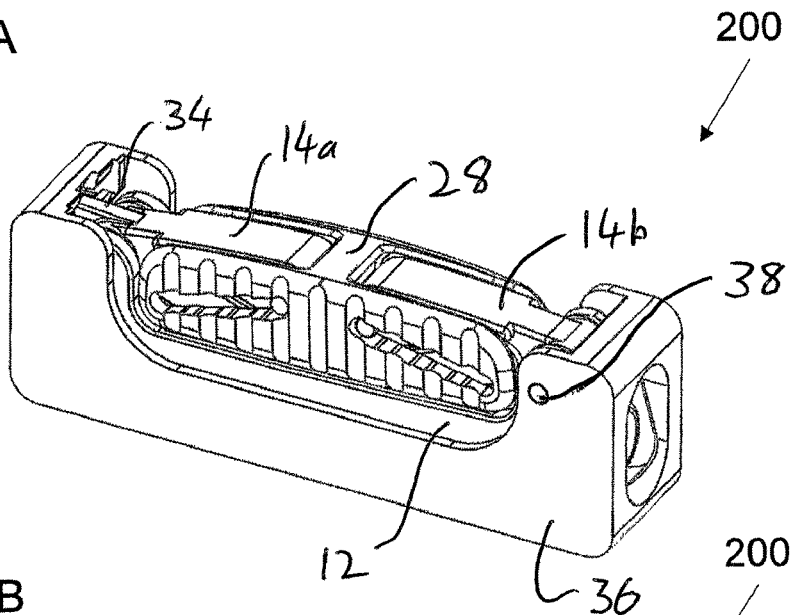
FIG. 5A is an isometric view of a second variant implementation of the implant of FIGS. 1A-1C.
Figure 5B:
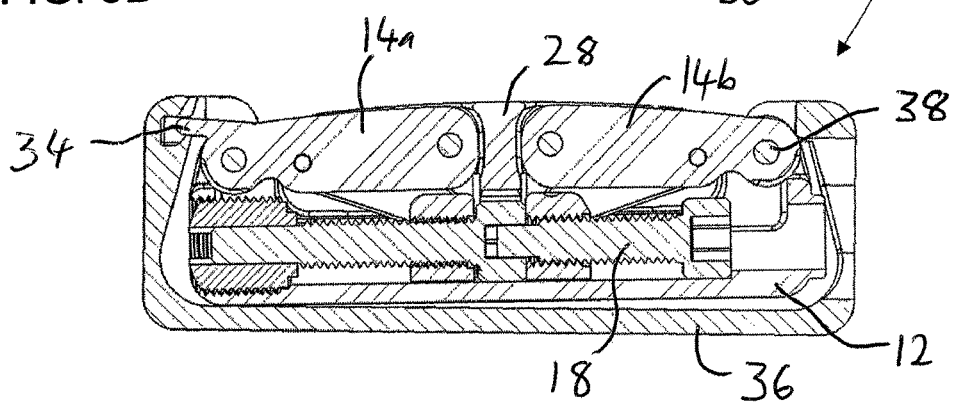
FIGS. 5B and 5C are cross-sectional views taken through the implant of FIG. 5A, shown in a low-profile insertion state and a fully-expanded state, respectively.
Figure 5C:
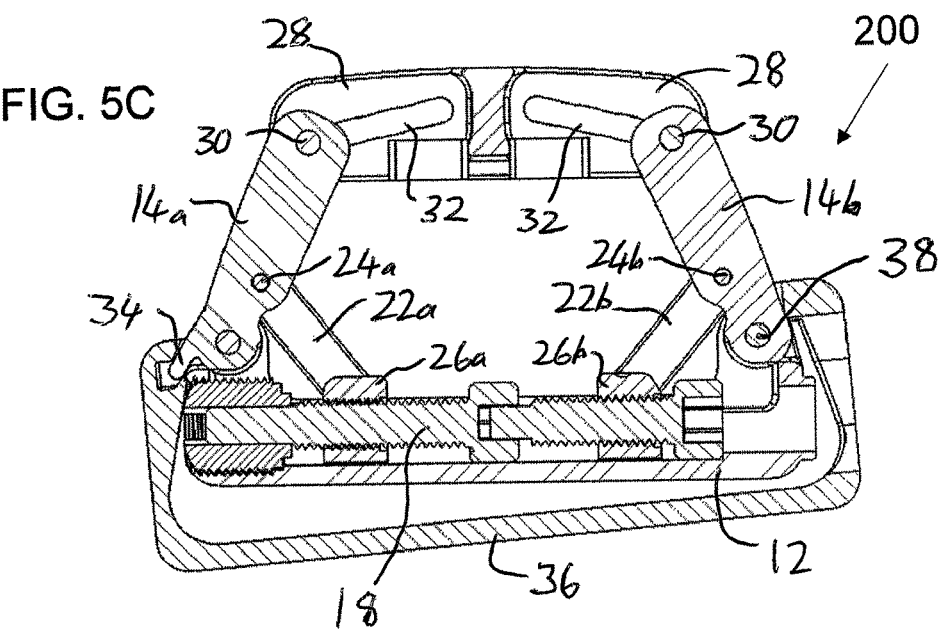
Figure 6A:
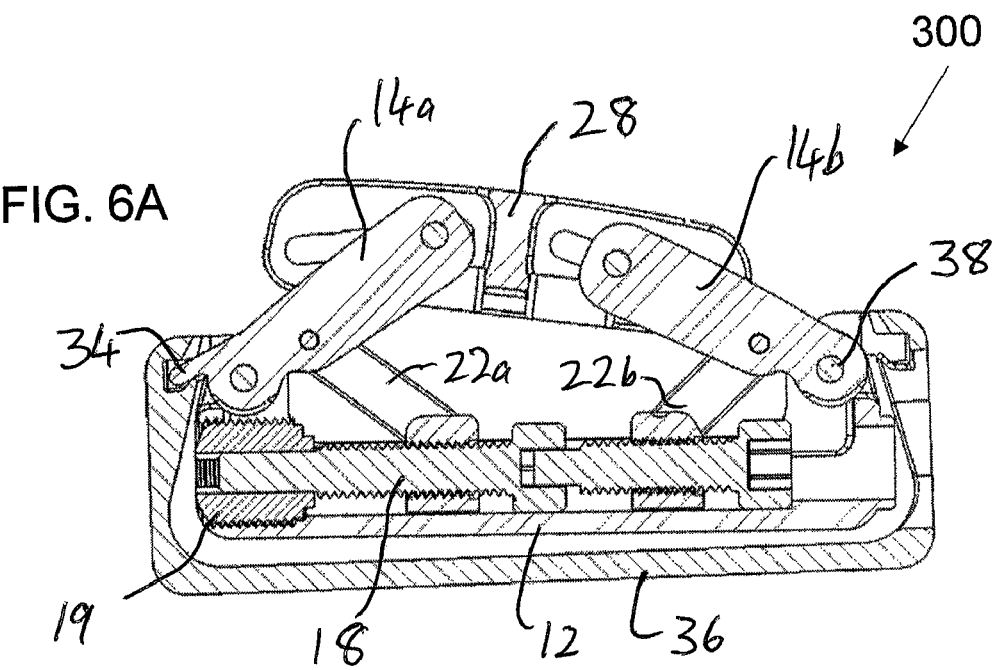
FIGS. 6A and 6B are cross-sectional views taken through a further variant of the implant of FIG. 5A, shown in a partially-expanded state and a fully-expanded state, respectively.
Figure 6B:
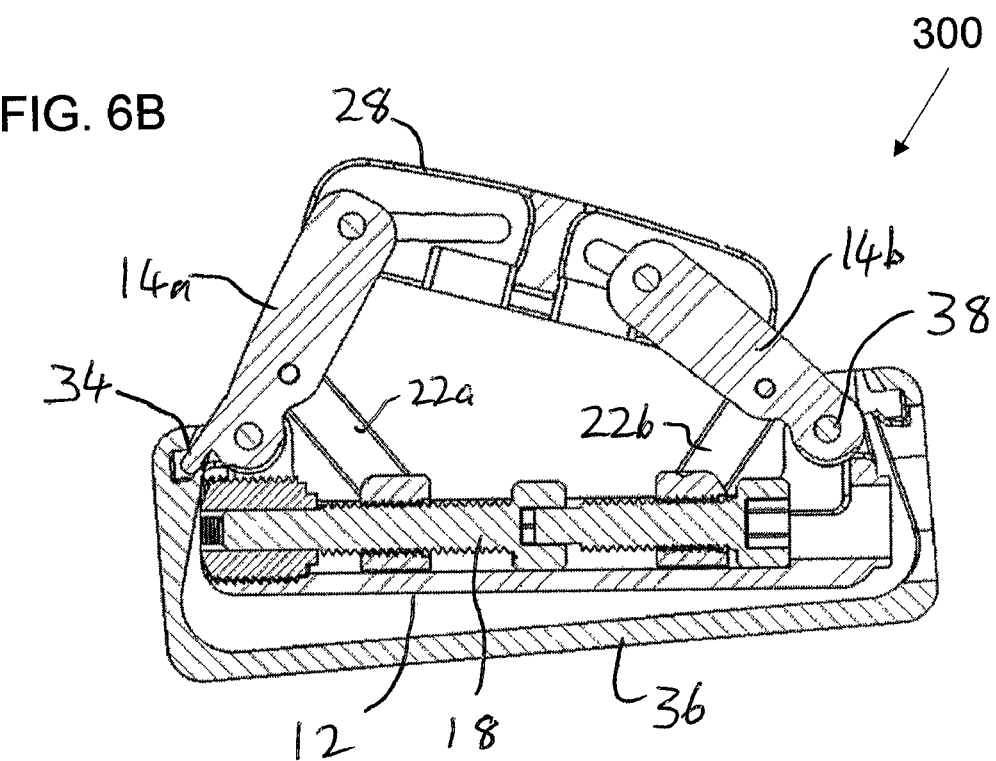
Figure 7A:
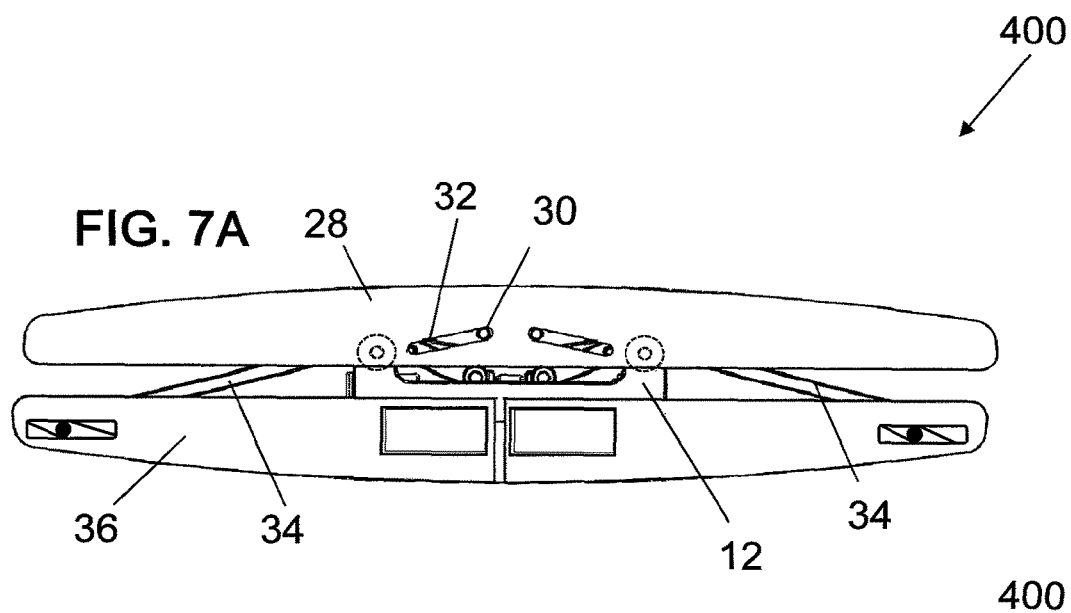
FIGS. 7A and 7B are schematic side views of a further variant implementation of an expanding implant shown in a partially-expanded state and a fully-expanded state, respectively.
Figure 7B:
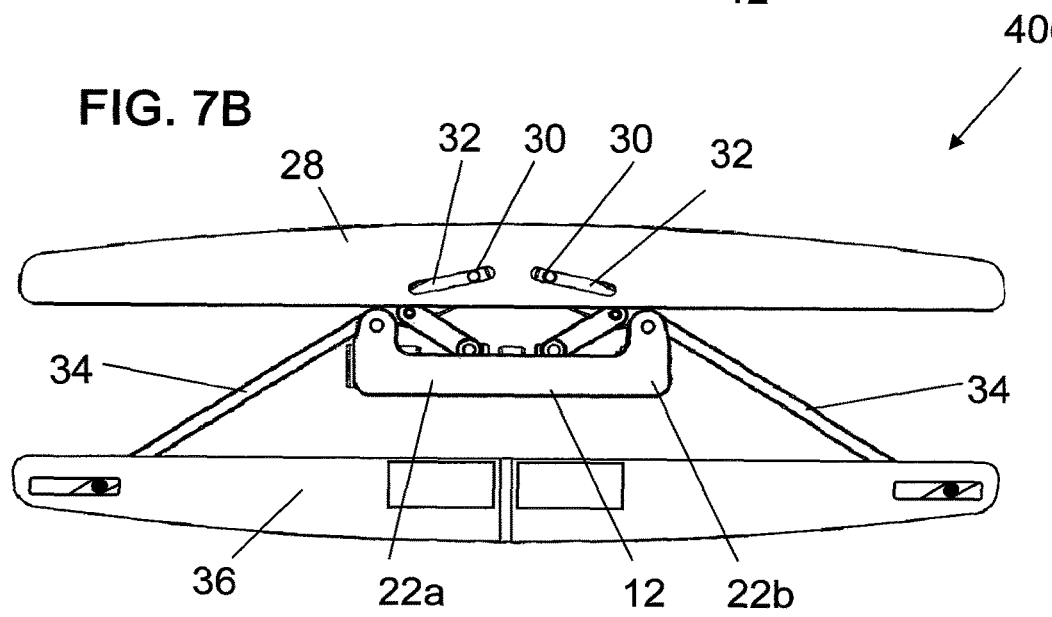
Figure 9A:
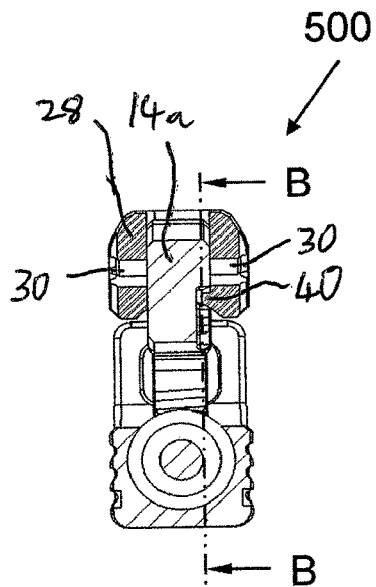
FIG. 9A is a cross-sectional view taken along the line A-A in FIG. 8B.
Figure 9B:
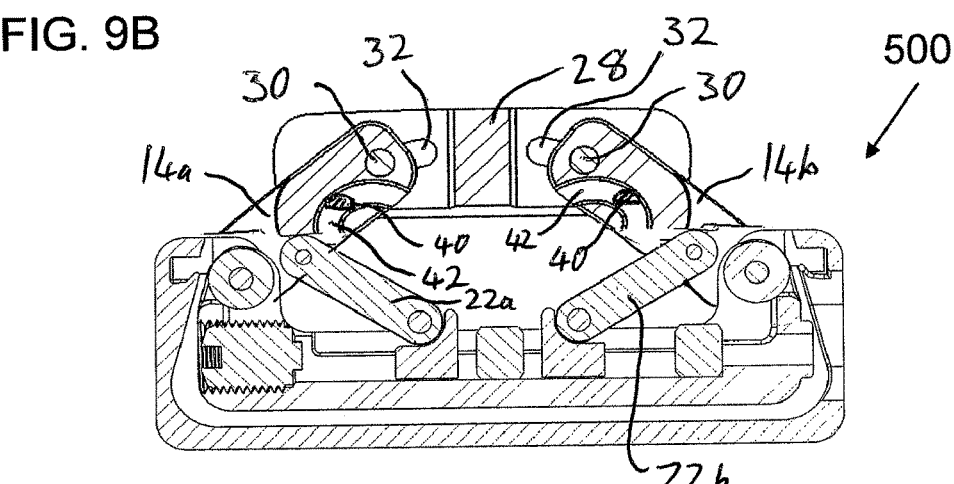
FIGS. 9B and 9C are cross-sectional views taken along the line B-B in FIG. 9A with the implant shown in a partially-expanded state and a fully-expanded state, respectively.
Figure 9C:
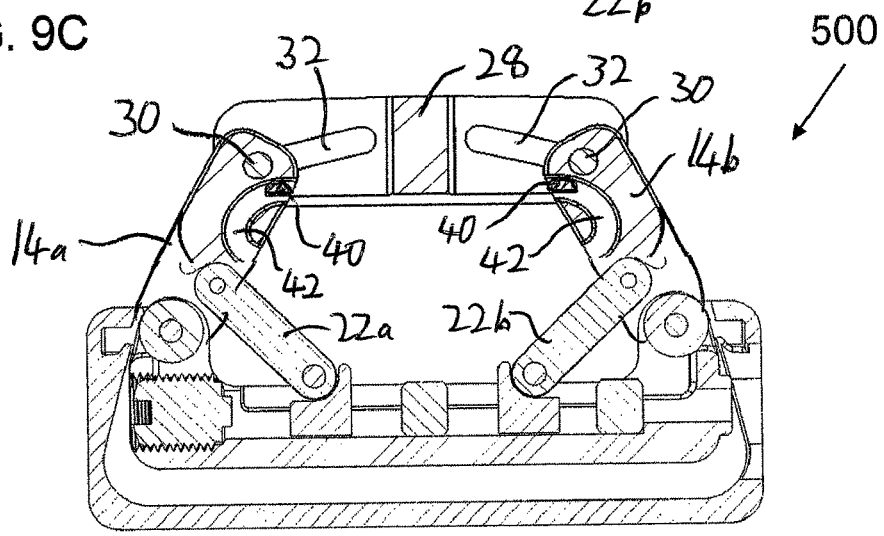
Figure 10A:
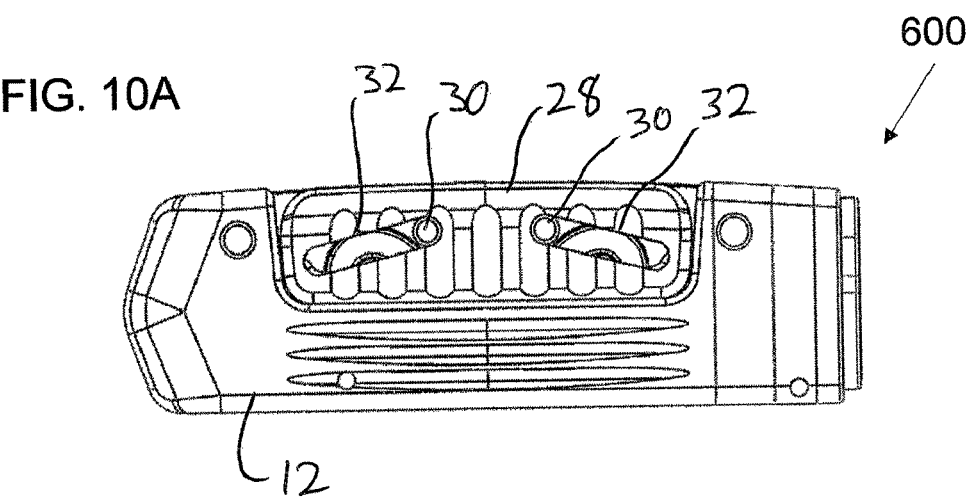
FIGS. 10A-10C are side views of an expanding implant employing the arrangement for limiting sliding of a bridging element in the context of a worm-gear-actuated implant, the implant being shown in a low-profile insertion state, a partially-expanded state and a fully-expanded state, respectively.
Figure 10B:
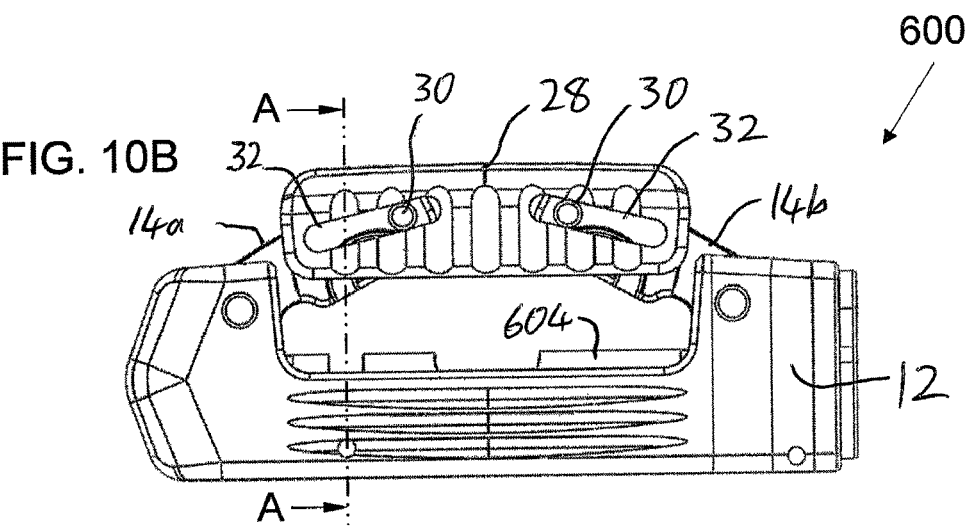
Figure 10C:
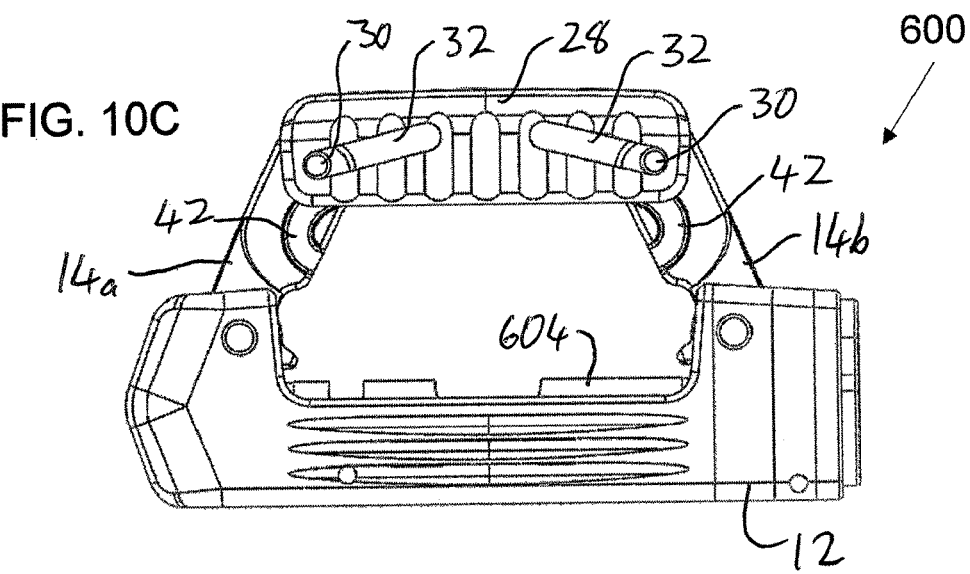
Figure 11A:
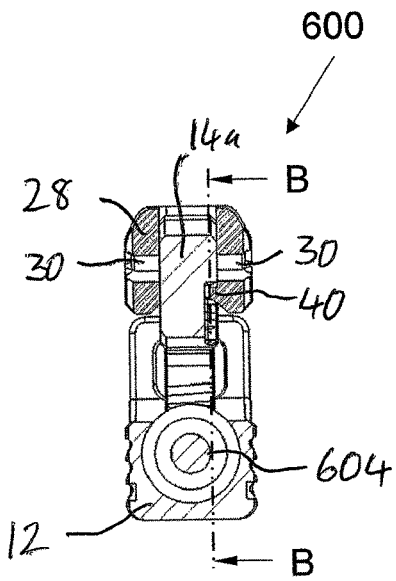
FIG. 11A is a cross-sectional view taken along the line A-A in FIG. 10B.
Figure 11B:
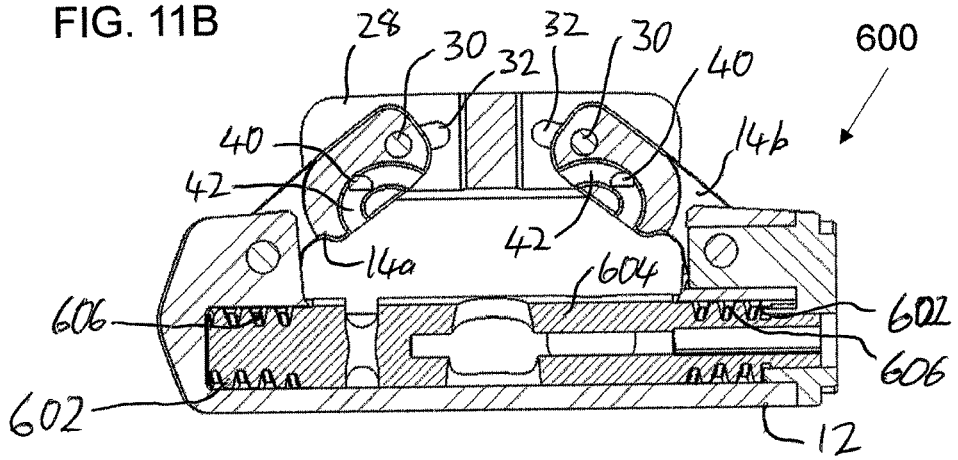
FIGS. 11B and 11C are cross-sectional views taken along the line B-B in FIG. 11A with the implant shown in a partially-expanded state and a fully-expanded state, respectively.
Figure 11C:
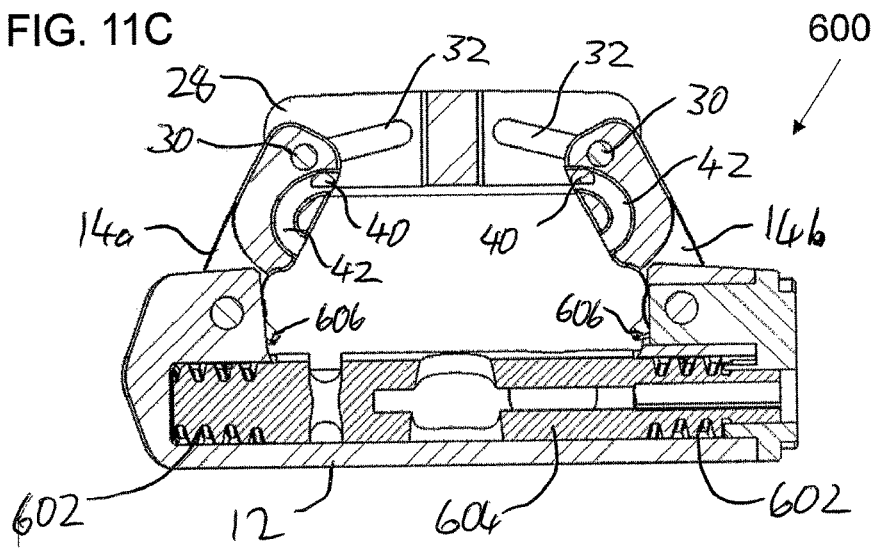

Clearly, these considerations apply equally to the second arm 14b and its corresponding actuating components. In implant 10 as illustrated here, dimensions $L_1$, $L_2$ and $L_3$ are the same for both arms 14a and 14b and the thread pitch of the two portions of bolt 18 is the same, resulting in symmetrical opening of the two arms. Referring briefly to FIGS. 4A-4C, these show an alternative implementation of an implant, generally designated 100, which is generally structurally and functionally similar to implant 10, with analogous elements labeled similarly. In this case, second actuator linkage 22b is shorter than first actuator linkage 22a, resulting in lesser mechanical amplification of the opening of second arm 14b and a corresponding asymmetric opening of implant 100, as seen in FIGS. 4B and 4C. It should be noted that the degree of mechanical amplification can additionally, or alternatively, be varied by moving the location of pivot point 24b along arm 14b and/or employing arms of differing lengths.

The actuator configuration described thus far is applicable to a range of implant forms, particularly where a base supports at least two arms which are deployed simultaneously in opposite angular motions, including cases where the arms are initially convergent or divergent, and including cases with and without bridging elements extending between the arms. In one particularly preferred set of applications as exemplified by the drawings herein, a rigid bridging element 28 bridges between first arm 14a and second arm 14b. In this case, bridging element 28 is preferably engaged with arms 14a and 14b via a pin-in-slot engagement, here shown as a pin 30 associated with an end portion of each arm that engages a slot 32 formed in bridging element 28. Most preferably, a double-pin-in-slot engagement is provided, with two pins engaged in non-parallel slots, as will be described in detail below with reference to FIGS. 8A-11C.

It should be noted that references herein to "arms", "linkages" etc. refer to functional elements which may, for design purposes, be implemented as either single or double structures. For example, referring to the exploded view of FIG. 3, it will be noted that arms 14a and 14b are shown as single elements while linkages 22a and 22b are bilaterally attached pairs of linkages on either side of the arms. Similarly, base 12 and bridging element 28 are shown here as two-sided elements internally connected. These structures could be reversed, for example, employing a pair of arms for each "arm" structure and a single linkage for each of linkages 22a and 22b, as will be appreciated by one ordinarily skilled in the art.

Figure 3:
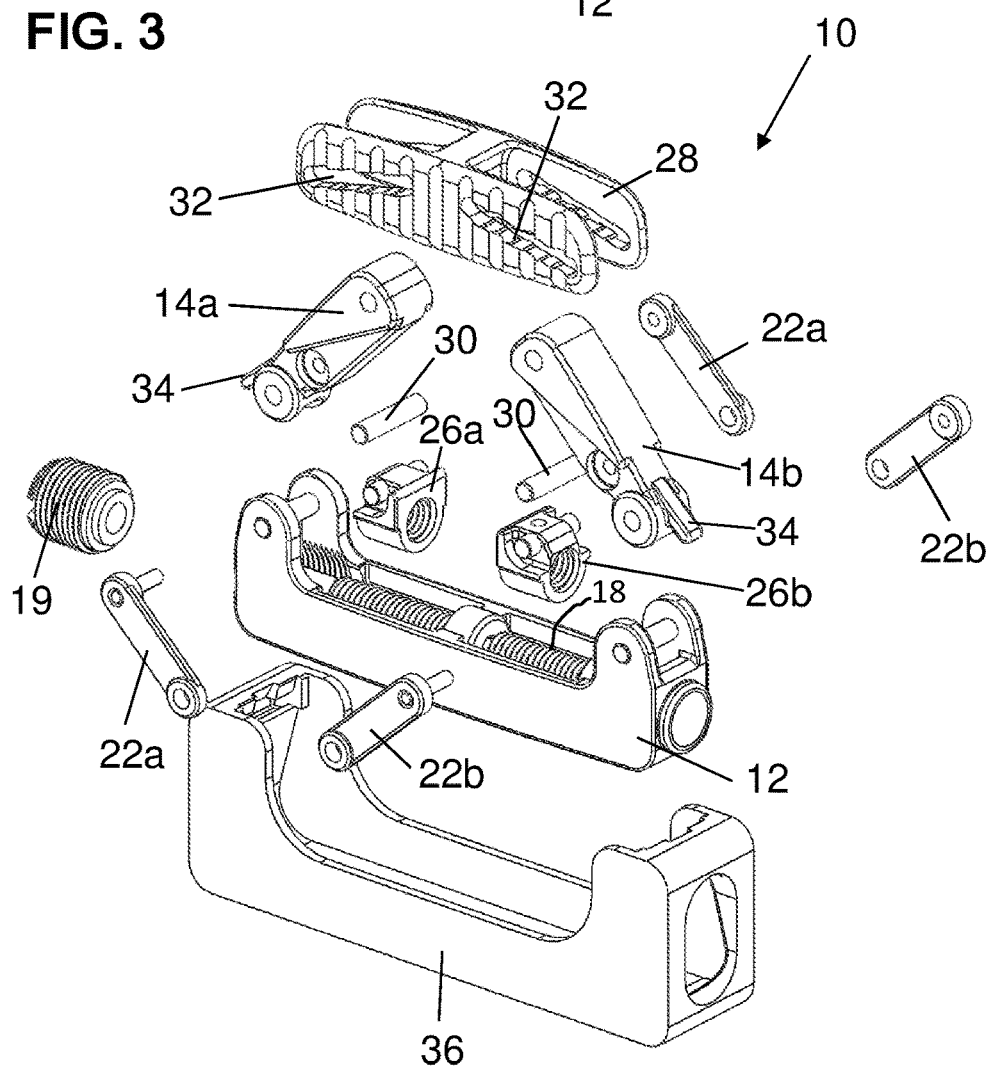
FIG. 3 is an exploded isometric view showing the parts of the implant of FIGS. 1A-1C.

As also best seen in FIG. 3, mounting of bolt 18 within base 12 is preferably achieved at least in part by a rotary bearing 19 which is inserted into the distal end of base 12. For simplicity of assembly, rotary bearing 19 may itself have an external thread which engages a corresponding threaded region within the distal end of base 12. At the other end, bolt 18 is preferably inset from a proximal opening of the implant sufficiently to leave an open channel for introduction of filler material into an inner volume of the implant after expansion.

Turning now again to FIGS. 1A-3, a second aspect of the present invention is independent of the actuator mechanism employed to displace the arms and relates to a case in which at least one arm 14a is hinged to base 12 at a hinge location 16a and extends from the hinge location in a direction of extension that initially forms a first angle, in this case close to zero, to a length of base 12. First arm 14a has a rear projection 34 projecting beyond the hinge location in a direction away from the direction of extension. The rear projection 34 engages a displaceable portion 36 of the implant so that, when an actuator is operated to rotate first arm 14a from its initial state towards a deployed state at a second, larger angle to the length, rear projection 34 causes displacement of displaceable portion 36 relative to base 12.

Figure 1C:
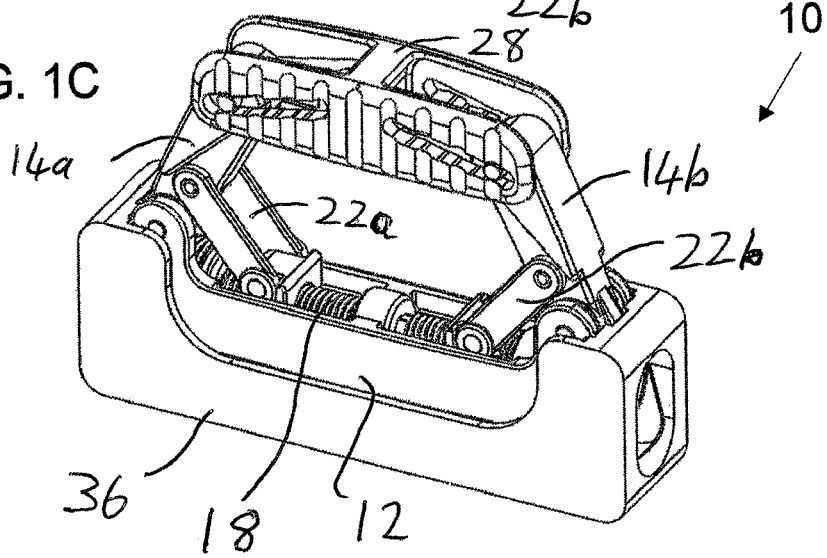

In the example of implant 10 (FIGS. 1A-3) and implant 100 (FIGS. 4A-4C), both arms 14a and 14b are formed with rear projections 34 engaging displaceable portion 36 to that the rotation of the arms generates displacement of displaceable portion 36 at both ends of the implant. In the case of implant 10, the symmetrical rotation of the arms results in symmetrical displacement of displaceable portion 36, as best seen in FIGS. 1C and 2C. In the case of implant 100, the asymmetric rotation of the arms typically generates asymmetric displacement of displaceable portion 36, unless this asymmetry is compensated for, for example by employing a longer rear projection (not shown).

Engagement between rear projections 34 and displaceable portion 36 may be any suitable form of mechanical engagement. In the particularly simple implementation illustrated here, rear projections 34 are a simple projecting tab with a rounded end that engages a suitably shaped recess (slot or pocket) in displaceable portion 36. Other forms of engagement, such as one or more gear teeth engaging a rack, or a pin-in-slot engagement, may also be used, but this simple tab-in-socket engagement is believed to be sufficient for many implementations.

FIGS. 5A-6B show further variant implementations of an implant differing from those above by the deployment of displaceable portion 36. Specifically, in these implementations, displaceable portion 36 is pivotally linked to base 12 at a hinge, in this case implemented by engagement with an extended hinge pin 38 forming the hinged connection between second arm 14b and base 12 at hinge location 16b (see FIG. 5A). In this case, only arm 14a is formed with rear projection 34, and displacement of displaceable portion 36 is a rotary motion. In the case of implant 200 of FIGS. 5A-5C, the remainder of the mechanism is a symmetrical mechanism, equivalent to that of implant 10 above. In the case of implant 300 of FIGS. 6A and 6B, the remainder of the mechanism is an asymmetrical mechanism, equivalent to that of implant 100 above. In all other respects, implants 200 and 300 are fully analogous in structure and function to the implants described above.

In FIGS. 1A-6B, displaceable portion 36 is shown implemented as a casing, at least partially encompassing base 12. It should be noted that this form is non-limiting and that, depending upon the intended application, displaceable portion may be implemented in various different forms. For example, in various cases, an open frame may be superior to allow bone ingrowth into the deployed implant.

Additionally, it should be noted that the same operational principles may be applied to implants with very different geometry. For example, in contrast to the above embodiments in which rear projections 34 are short (typically less than 20%, and preferably less than 10% of the length of the corresponding arm), an alternative implementation illustrated schematically in FIGS. 7A and 7B employs rear projections that extend to a length greater than the inward-directed part of the arms. In this case, both bridging element 28 and displaceable element 36 are preferably significantly longer than base 12, and engagement between rear projections 34 and displaceable element 36 are implemented as pin-in-slot engagements.

Turning now to a third aspect of the present invention, in the above embodiments, as well as other implant structures in which a bridging element bridges between two arms hingedly mounted to a base, engagement between the bridging element and the arms is typically achieved through a pin-in-slot engagement. In a fully-closed, low-profile state and a fully-open state, the pins are typically at the end of the slots and the position of the bridging element is well defined. However, at partially-deployed intermediate positions, there is potential for sliding motion of the bridging element parallel to the length of the base.

In applications where such freedom of sliding motion is undesirable, a third aspect of the present invention serves to limit such sliding motion. Referring specifically to FIGS. 8A-9C, these illustrate an implant 500 which is similar in structure and function to implant 10 described above, with analogous elements labeled similarly. Thus, implant 500 includes a base 12, hinged arms 14a and 14b, and an actuator (bolt 18 not visible in these views and actuator linkages 22a and 22b) operatively linked to the arms and operable to rotate the first and second arms from their initial state in opposing angular motion towards a final state. Rigid bridging element 28 bridges between first arm 14a and second arm 14b such that deployment of the first and second arms from the initial state towards the final state displaces the bridging element away from the base.

Implant 500 differs from implant 10 in that engagement between bridging element 28 and at least the first arm 14a is via a double-pin-in-slot engagement with two non-collinear pins engaged in non-parallel slots. Thus, in addition to pin 30 that projects from arm 14a to engage slot 32 in bridging element 28, bridging element 28 also features a projecting pin 40 that is engaged with a slot 42 formed in arm 14a, as best seen in the cross-sectional view of FIGS. 9B and 9C.

It will be noted that the desired relative motion of the arms and the bridging element as the implant expands is a compound motion made up of displacement plus rotation. As a result, the trace of each point on the arm passing across the surface of the bridging element follows a unique path, and vice versa for points on the bridging element passing across the surface of the arm. By forming an additional pin projecting from one of these surfaces, and a complementary slot corresponding to the desired path to be followed by that pin on the facing surface, it is possible to limit, and typically substantially eliminate, unwanted sliding motion of the bridging element. The slots are necessarily of different shapes, and thus inherently "non-parallel".

The above principle may be implemented in numerous ways, including providing both pins projecting from the arm and a corresponding pair of non-parallel slots in the bridging element. However, it has been found particularly effective for certain implementations of the present invention to provide pin 40 projecting (in this case inwards) from bridging element 28, at or near a lower edge of the bridging element. This position helps to ensure overlap with arm 14a during most if not all of the range of motion. The corresponding shape of slot 42 is a generally arcuate channel of non-uniform curvature, as may be derived in a straightforward manner from trigonometric calculations over the range of angular motion of arm 14a. Pin 40 need not be circular, and in fact is shown here as a flattened rhombus shape, chosen for reasons of ease of manufacture.

In principle, provision of this double pin-in-slot engagement on only one of arms 14a and 14b would be sufficient to eliminate the undesired sliding. However, where motion of the two arms is synchronous in a fixed proportion (symmetrically or asymmetrically), it is typically preferable to provide double pin-in-slot engagement between bridging element 28 and each of arms 14a and 14b, as illustrated here. In cases of individually adjustable arms (such as certain examples mentioned in the aforementioned WO2015087285 publication), the double pin-in-slot engagement should be used on only one arm.

Although certain reference numerals have been omitted in order to increase intelligibility of the drawings, implant 500 also includes all features and functionality described above with reference to implant 10, including the threaded-bolt actuator with mechanical amplification, and the rear projections actuating the displaceable element. All such features will be fully understood by reference to the drawings and description above in the context of implant 10.

Turning now to FIGS. 10A-11C, these illustrate the application of the double pin-in-slot engagement in the context of an implant 600 actuated by a worm-gear engagement between a worms 602 formed in a worm-rod 604 engaging teeth 606 associated with each of two arms 14a and 14b. Further details of various implants of this type may be found in WO2015087285. The features defining the double pin-in-slot engagement for one or both of arms 14a and 14b are identical to those described in the context of implant 500 above, including pin 30 in slot 32 and pin 40 in slot 42, all as described above.

It should be noted that the various implants described herein may be used in any and all orthopedic applications in which an expanding implant is required, and are particularly suitable for various minimally invasive spinal surgery (MISS) techniques, for intra-body or inter-body placement, and in various orientations and approach directions. Without detracting from the generality of the above, various applications of particular significance employ the implants deployed intervertebrally oriented so as to expand axially, thereby achieving restoration of intervertebral height and/or correction of lordotic angle or scoliosis misalignment. Other applications of particular significance employ the implant deployed intervertebrally with expansion within the plane of the disc. In each case, the appropriate surfaces are modified according to the intended application by addition of bone-purchase features, windows for filling with biocompatible filler and/or osseous integration, all as will be clear to a person having ordinary skill in the art.

It will be appreciated that the above descriptions are intended only to serve as examples, and that many other embodiments are possible within the scope of the present invention as defined in the appended claims.

What is claimed is:

1. An implant comprising:
   (a) a base;
   (b) a first arm hinged to said base at a first hinge location and extending from said first hinge location in a direction of extension;
   (c) a second arm hinged to said base at a second hinge location and extending from said second hinge location in a direction of extension, said first and second arms assuming an initial state;
   (d) an actuator operatively linked to said first and second arms and operable to rotate said first and second arms from said initial state in opposing angular motion towards a final state; and
   (e) a rigid bridging element bridging between said first arm and said second arm such that deployment of said first and second arms from said initial state towards said final state displaces said bridging element away from said base, wherein engagement between said bridging element and at least one of said first and second arms is via a double pin-in-slot engagement with two non-collinear pins engaged in respective non-parallel slots.

2. The implant of claim 1, wherein said double pin-in-slot engagement comprises a first pin projecting from said first arm engaging a slot formed in said bridging element, and a pin projecting from said bridging element engaging a slot formed in said first arm.

3. The implant of claim 1, wherein engagement between said bridging element and each of said first and second arms is via a double pin-in-slot engagement with two non-collinear pins engaged in respective non-parallel slots.

4. The implant of claim 1, wherein said actuator comprises:
   (a) a threaded bolt extending within said base and mounted so as to be rotatable about a central axis of said threaded bolt;
   (b) a first actuator linkage hinged to said first arm and hinged to a first rider engaged with said threaded bolt; and
   (c) a second actuator linkage hinged to said second arm and hinged to a second rider engaged with said threaded bolt,
   such that rotation of said threaded bolt causes displacement of said first and second riders, and hence of said first and second actuator linkages to generate motion of said first and second arms.

5. The implant of claim 4, wherein said first actuator linkage and said second actuator linkage are of different lengths such that said bridging element opens asymmetrically away from said base.

6. The implant of claim 4, wherein said directions of extension of said first and second arms being convergent.

7. The implant of claim 6, wherein said first arm further comprises a rear projection projecting beyond said hinge location in a direction away from said direction of extension, the implant further comprising a displaceable portion engaged with said rear projection such that rotation of said threaded bolt causes displacement of said bridging element in a first direction and of said displaceable portion in a second direction generally opposite to said first direction.

8. The implant of claim 6, wherein each of said first and second arms further comprises a rear projection projecting beyond said hinge location in a direction away from said direction of extension, the implant further comprising a displaceable portion engaged with said rear projections such that rotation of said threaded bolt causes displacement of said bridging element in a first direction and of said displaceable portion in a second direction generally opposite to said first direction.

9. The implant of claim 4, wherein said threaded bolt includes a first portion with a right-handed thread and a second portion with a left-handed thread.

10. An implant comprising:
    (a) a base;
    (b) a first arm hinged to said base;
    (c) a second arm hinged to said base;

(d) a threaded bolt extending within said base and mounted so as to be rotatable about a central axis of said threaded bolt;

(e) a first actuator linkage hinged to said first arm and hinged to a first rider engaged with said threaded bolt;

(f) a second actuator linkage hinged to said second arm and hinged to a second rider engaged with said threaded bolt, such that rotation of said threaded bolt causes displacement of said first and second riders, and hence of said first and second actuator linkages to generate motion of said first and second arms; and (g) a bridging element bridging between said first arm and said second arm.

11. The implant of claim 10, wherein said bridging element is a rigid bridging element engaged with said first and second arms by a pin-in-slot engagement.

12. The implant of claim 11, wherein said pin-in-slot engagement is a double-pin-in-slot engagement with two pins engaged in non-parallel slots.

13. The implant of claim 11, wherein said first actuator linkage and said second actuator linkage are of different lengths such that said bridging element opens asymmetrically away from said base.

14. The implant of claim 11, wherein each of said first and second arms is hinged to said base at a hinge location, and extends from said hinge location in a direction of extension, said directions of extension of said first and second arms being convergent.

15. The implant of claim 14, wherein said first arm further comprises a rear projection projecting beyond said hinge location in a direction away from said direction of extension, the implant further comprising a displaceable portion engaged with said rear projection such that rotation of said threaded bolt causes displacement of said bridging element in a first direction and of said displaceable portion in a second direction generally opposite to said first direction.

16. The implant of claim 14, wherein each of said first and second arms further comprises a rear projection projecting beyond said hinge location in a direction away from said direction of extension, the implant further comprising a displaceable portion engaged with said rear projections such that rotation of said threaded bolt causes displacement of said bridging element in a first direction and of said displaceable portion in a second direction generally opposite to said first direction.

17. The implant of claim 10, wherein said threaded bolt includes a first portion with a right-handed thread and a second portion with a left-handed thread.

* * * * *